United States Patent [19]

Sitzmann et al.

[11] Patent Number: 4,831,186
[45] Date of Patent: May 16, 1989

[54] PENTAFLUOROSULFANYL POLYNITROALIPHATIC UREA, MONOCARBAMATE, AND DICARBAMATE EXPLOSIVE COMPOUNDS

[75] Inventors: Michael E. Sitzmann, Adelphi; William H. Gilligan, Ft. Washington, both of Md.

[73] Assignee: The United States of America as represented by the Secretary of the Navy, Washington, D.C.

[21] Appl. No.: 213,038

[22] Filed: Jun. 24, 1988

[51] Int. Cl.$^4$ .......................................... C07C 125/065
[52] U.S. Cl. .................................................. 560/148
[58] Field of Search ...................... 560/148; 564/39, 59

[56] References Cited

U.S. PATENT DOCUMENTS 3,850,978 11/1974 Gilligan et al. ........................ 564/59
4,449,000 5/1984 Sitzmann et al. ................... 568/590

OTHER PUBLICATIONS

Chem. Ber., 117, 1707–1725 (1984), Thrasher et al.
Inorganic Chemistry, 21, 1616 (1982), Thrasher et al.
Journal of Inorganic Nuclear Chemistry, Supplement 1976, pp. 33–36, Duncan et al.

Primary Examiner—Donald B. Moyer
Assistant Examiner—Julie K. Parker
Attorney, Agent, or Firm—Kenneth E. Walden; Roger D. Johnson

[57] ABSTRACT

Pentafluorosulfanyl polynitroaliphatic explosive compounds of the formulas

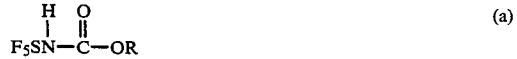

(a)

where R is $-CH_2C(NO_2)_2CH_3$, $-CH_2CH_2C(NO_2)_3$, $-CH_2CF(NO_2)_2$, and $-CH_2C(NO_2)_3$;

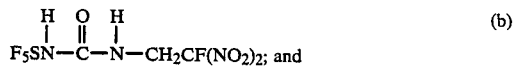

(b)

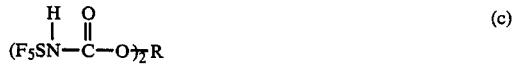

(c)

where R is $-CH_2C(NO_2)_2CH_2-$, $-CH_2C(NO_2)_2CH_2OCH_2OCH_2C(NO_2)_2CH_2-$, $-CH_2CH_2N(NO_2)CH_2CH_2N(NO_2)CH_2CH_2-$, and $-CH_2CH_2N(NO_2)CH_2C(NO_2)_2CH_2CH_2CH_2-$.

5 Claims, No Drawings

PENTAFLUOROSULFANYL POLYNITROALIPHATIC UREA, MONOCARBAMATE, AND DICARBAMATE EXPLOSIVE COMPOUNDS

BACKGROUND OF THE INVENTION

This invention relates to explosives and more particularly to polynitro organic explosives.

E. F. Witucki and M. B. Frankel, J. Chem. and Eng. Data, 24, 382 (1979), reported preparation of 2-fluoro-2,2-dinitroethyl pentafluorothioacetate from 2-fluoro-2,2-dinitroethanol and pentafluorothioacetyl chloride. The acetyl chloride was chosen as the —SF$_5$ starting material because of its availability from SF$_5$Cl and ketene. E. F. Wituck and M. B. Frankel, Rockwell International UCRL report 13809 (1978), describe 2-fluoro-2,2-dinitroethyl pentafluorothioacetate as a dense, thermally stable, insensitive liquid.

We have recently prepared other polynitroaliphatic esters of pentafluorothioacetic acid using the Witucki et al., method and have found them to be liquids or very low melting solids. For instance:

| Ester | M.P. (° C.) |
| --- | --- |
| 2,2-dinitropropyl pentafluorothioacetate | 22 |
| 3-fluoro-3,3-dinitropropyl pentafluorothioacetate | 28 |
| 3,3,3-trinitropropyl pentafluorothioacetate | 32 |

Thus, like the prior art 2-fluoro-2,2-dinitroethyl pentafluorothioacetate, these novel polynitroaliphatic esters of pentafluorothioacetic acid are limited to liquids or very low melting solids. This is a disadvantage because many applications require high melting solid explosives. Therefore, it would be desirable to have available higher melting pentafluorothio (SF$_5$) explosives in order to provide a greater choice of physical properties for these types of compounds.

In U.S. Navy Case Ser. No. 71,604 entitled "Pentafluorothio Polynitroaliphatic Explosives," filed at the same time as this application by the same inventive entity (Michael E. Sitzmann and William H. Gilligan), compounds are disclosed and claimed which appreciably extend the range of physical properties available in SF$_3$ explosives but they suffer a disadvantage in that they are synthesized from 2-pentafluorothioethanol. The disadvantage of using 2-pentafluorothioethanol is that it contains appreciable carbon and hydrogen in addition to the SF$_3$ group. Thus, in order to attain maximum energy output, any polynitroaliphatic derivative of 2-pentafluorothioethanol must contain extra oxidant to totally combust this carbon and hydrogen to CO$_2$, H$_2$O, and HF. Also this carbon and hydrogen will tend to dilute the effect of the SF$_5$ group toward increasing the density of the polynitroaliphatic explosive. Therefore it would often be advantageous to employ an SF$_5$ starting material that contains little, if any, carbon and hydrogen along with the SF$_5$ group.

SUMMARY OF THE INVENTION

Accordingly, an object of this invention is to provide new eneergetic explosive compounds.

Another object of this invention is to provide new pentafluorothio polynitroaliphatic explosives.

A further object of this invention is to provide new high melting pentafluorothio polynitroaliphatic explosives.

Still another object of this invention is to provide new high energy, high density explosives.

A still further object of this invention is to provide new high energy explosives having good thermal stabilities.

These and other objects of this invention are achieved by providing explosives compounds of the formula:

where R is —CH$_2$C(NO$_2$)$_2$CH$_3$, —CH$_2$CH$_2$C(NO$_2$)$_3$, —CH$_2$CF(NO$_2$)$_2$, or —CH$_2$C(NO$_2$)$_3$;

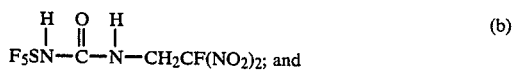

where R is —CH$_2$C(NO$_2$)$_2$CH$_2$—, —CH$_2$C(NO$_2$)$_2$CH$_2$OCH$_2$C(NO$_2$)$_2$CH$_2$—, —CH$_2$CH$_2$N(NO$_2$)CH$_2$CH$_2$N(NO$_2$)CH$_2$CH—, or —CH$_2$CH$_2$N(NO$_2$)CH$_2$C(NO$_2$)$_2$CH$_2$CH$_2$CH$_2$—.

DETAILED DESCRIPTION OF THE PREFERRED EMBODIMENT

The explosives of the present invention are pentafluorothio polynitroaliphatic monocarbamate, urea, and dicarbamate compounds which are synthesized from pentafluorosulfanyl isocyanate (F$_5$SN=C=O). Pentafluorosulfanyl isocyanate may be prepared according to the method described in example 1.

The monocarbamate compounds are produced by reacting pentafluorosulfanyl isocyanate, F$_5$SN=C=O, with the appropriate polynitroaliphatic alcohol:

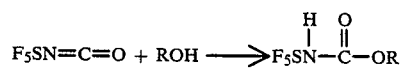

where R is —CH$_2$C(NO$_2$)$_2$CH$_3$, —CH$_2$CH$_2$C(NO$_2$)$_3$, —CH$_2$CF(NO$_2$)$_2$, or —CH$_2$C(NO$_2$)$_3$.

Specifically, N-pentafluorosulfanyl-2,2-dinitropropyl carbamate,

is prepared by reacting pentafluorosulfanyl isocyanate with 2,2-dinitropropanol, CH$_3$C(NO$_2$)$_2$CH$_2$OH, according to the method described in example 2. N-pentafluorosulfanyl-3,3,3-trinitropropyl carbamate,

is prepared by reacting pentafluorosulfanyl isocyanate with 3,3,3-trinitropropanol, C(NO$_2$)$_3$CH$_2$CH$_2$OH, according to the method described in example 3.

N-pentafluorosulfanyl-2-fluoro-2,2-dinitroethyl carbamate,

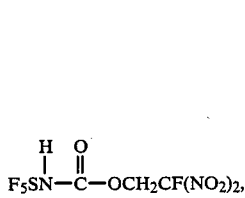

is prepared by reacting pentafluorosulfanyl isocyanate with 2-fluoro-2,2-dinitroethanol, $CF(NO_2)_2CH_2OH$, according to the method described in example 4.

N-pentafluorosulfanyl-2,2,2-trinitroethyl carbamate,

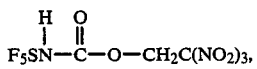

is prepared by reacting pentafluorosulfanyl isocyanate with 2,2,2-trinitroethanol, $C(NO_2)_3CH_2OH$, according to the method described in example 5.

N-(pentafluorosulfanyl)-N'-(2-fluoro-2,2-dinitroethyl)urea is prepared by reacting pentafluorosulfanyl isocyanate with 2-fluoro-2,2-dinitroethylamine,

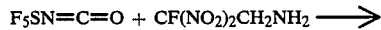

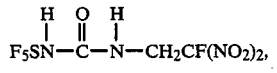

according to the method described in example 6.

The dicarbamates are produced by reacting pentafluorosulfanyl isocyanate, $F_5SN\!=\!C\!=\!O$, with the appropriate diol

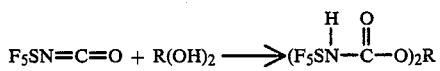

where R is $-CH_2C(NO_2)_2CH_2-$, $-CH_2C(NO_2)_2C\-H_2OCH_2OCH_2C(NO_2)_2CH_2-$, $-CH_2CH_2N(NO_2)CH_2CH_2N(NO_2)CH_2CH_2-$ or $-CH_2CH_2N(NO_2)CH_2C(NO_2)_2CH_2CH_2CH_2-$.

Specifically, N,N'-bis(pentafluorosulfanyl)-2,2-dinitropropane-1,3-dicarbamate,

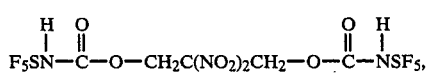

is prepared by reacting 2 moles of pentafluorosulfanyl isocyanate with each mole of 2,2-dinitropropane-1,3-diol, $HOCH_2C(NO_2)_2CH_2OH$, according to the method described in example 7.

N,N'-bis(pentafluorosulfanyl)-2,2,8,8-tetranitro-4,6-dioxanonane-1,9-dicarbamate,

is prepared by reacting 2 moles of pentafluorosulfanyl isocyanate with each mole of 2,2,8,8-tetranitro-4,6-dioxanonane-1,9-diol, $HOCH_2C(NO_2)_2CH_2OCH_2OCH_2C(NO_2)_2CH_2OH$, according to the method described in example 8.

N,N'-bis(pentafluorosulfanyl)-3,6-dinitrazaoctane-1,8-dicarbamate,

is prepared by reacting 2 moles of pentafluorosulfanyl isocyanate with each mole of 3,6-dinitrazaoctane-1,8-diol, $HOCH_2CH_2N(NO_2)CH_2CH_2N(NO_2)CH_2C\-H_2OH$, according to the method described in example 9.

N,N'-bis(pentafluorosulfamyl)-3-nitraza-5,5-dinitrooctane-1,8-dicarbamate,

is prepared by reacting 2 moles of pentafluorosulfanyl isocyanate with each mole of 3-nitraza-5,5-dinitrooctane-1,8-diol, $HOCH_2CH_2N(NO_2)CH_2C(NO_2)_2CH_2CH_2CH_2OH$, according to the method described in example 10.

Acetonitrile is the preferred reaction solvent for the addition of polynitro alcohols and diols to pentafluorosulfanyl isocyanate although other solvents which are compatible with the isocyanate can be employed. For example, use of dichloroethane as the reaction solvent does give the carbamates but the reaction rate is slower (compare example 4 with example 5). An additional problem with dichloroethane is that the starting energetic diols are only slightly soluble in this solvent resulting in even slower reaction rates (compare example 7 with examples 8, 9 and 10).

One can look at N-pentafluorosulfanyl-3,3,3-trinitropropyl carbamate, with molecular formula $C_4H_5F_5N_4O_8S$, as an example of the high oxidant level attainable by combining pentafluorosulfonyl isocyanate and polynitroalcohols. Detonation calorimetry experiments indicated that sulfur is mainly converted to carbonyl sulfide in the detonation of $SF_5$ explosives, and therefore N-pentafluorosulfanyl-3,3,3-trinitropropyl carbamate contains sufficient oxidant to totally combust all carbon and hydrogen to $CO_2$, $H_2O$ and $HF$.

Compounds such as N-pentafluorosulfanyl-2-fluoro-2,2-dinitroethyl carbamate ($C_3H_3F_6N_3O_6S$) and N-pentafluorosulfanyl-2,2,2-trinitroethyl carbamate ($C_3H_3F_5N_4O_8S$) contain an appreciable excess of oxidant and can be used as oxidizers as well as explosives.

N-pentaflurosulfanyl-2-fluoro-2,2,-dinitroethyl carbamate and N,N'-bis(pentafluorosulfanyl)-2,2-dinitropropane-1,3-dicarbamate were selected as representatives for determination of crystal density (x-ray). Their crystal densities [2.04 (−40° C.) and 1.99 g/ml, respectively] show that the use of pentafluorosulfanyl isocyanate with polynitroaliphatic alcohols and diols can lead to very high density SF$_5$ explosives.

The use of pentafluorosulfanyl isocyanate as a starting material for SF$_5$ explosives offers a number of advantages. The isocyanate contains little carbon and no hydrogen and thus polynitroaliphatic explosives with high oxidant levels can be attained (some of them contain sufficient excess oxidant to be used as oxidizers). Also pentafluorosulfanyl isocyanate with polynitroalcohols and diols tends to give very high density SF$_5$ explosives (approximately 2.0 g/ml). In addition, the dicarbamates from pentafluorosulfanyl isocyanate and polynitroaliphatic diols have lowered solubility in organic solvents and thus are attractive candidates for use in formulations (plastic bonded explosives) where it is desirable that the solid explosive does not dissolve in the binder, or the plasticizer, or both. In fact, the dicarbamates are much less soluble in organic solvents than the monocarbamates and other SF$_5$ explosives. These dicarbamates also have appreciably higher melting points then any previously prepared SF$_5$ explosives thereby increasing the choice of physical properties for these types of compounds.

The general nature of the invention have been set forth, the following examples are presented as specific illustrations thereof. It will be understood that the invention is not limited to these specific examples, but is susceptible to various modifications that will be recognized by one of ordinary skill in the art.

The pentafluorosulfanyl isocyanate used in the following examples was supplied by Dr. Joseph S. Thrasher, University of Alabama (Tuscaloosa, Ala.).

Example 1 is quoted from an article by Joseph S. Thrasher, Jon L. Howell, and Alan F. Clifford entitled "Acylations of Pentafluorosulfanylamine, SF$_5$NH$_2$," Inorganic Chemistry, 1982, Vol. 21, No. 4, pages 1616+ at 1620. It provides a method by which the starting material pentafluorosulfanyl isocyanate (SF$_5$NCO) can be prepared.

EXAMPLE 1

Pentafluorosulfanyl isocyanate (SF$_5$NCO) (prior art)

"Preparation of SF$_5$NCO(O)F. In a typical reaction, 150 mmol each of NSF$_3$, COF$_2$, and HF were condensed into a 75-mL stainless-steel cylinder at −196° C. After the mixture was allowed to react for 5 days at room temperature, the volatile components were transferred onto a NaF scrubber while the reaction cylinder was held at −50° C. The product could then be removed from the cylinder as a colorless liquid. The SF$_5$NHC(O)F has a vapor pressure of ∼50 torr at 25° C. and spontaneously loses HF when in contact with glass or NaF. The yield (∼50%) was determined by removing the product to a NaF scrubber for several hours and then measuring the quantity of SF$_5$NCO recovered."

EXAMPLE 2

N-Pentafluorosulfanyl-2,2-dinitropropyl carbamate

Pentafluorosulfanyl isocyanate (2.2 g, 0.013 mole) was condensed at −78° C. (dry ice/acetone bath) into a flask containing 3.6 g (0.024 mole) of 2,2-dinitropropanol and 20 ml of dry 1,2-dichloroethane. A dry ice condenser with drierite tube was attached and the flask was allowed to warm to room temperature. After 24 hours at room temperature, the volatiles were removed to give a semisolid which was stirred with 25 ml of water to yield 3.3 g (80%) of solid, mp 92°–94° C. Crystallization from chloroform raised the melting point to 93°–94° C.; $^1$H NMR (CDCl$_3$): 2.23 (s, 3H), 5.08 (s, 2H), 7.97 (broad s, 1H); IR (KBr): 3290 (NH), 1765 (C=O), 1580 (NO$_2$), 1515 (amide II), 950–860 (SF$_5$) cm$^{-1}$.

Anal: Calcd for C$_4$H$_6$F$_5$N$_3$O$_6$S: C, 15.05; H, 1.89; F, 29.76; N, 13.16; S, 10.04. Found: C, 15.18; H, 1.84; F, 29.97; N, 13.00; S, 10.20.

EXAMPLE 3

N-Pentafluorosulfanyl-3,3,3-trinitropropyl carbamate

A flask containing a solution of 2.45 g (0.013 mole) of 3,3,3-trinotropropanol in 17 ml of dry 1,2-dichloroethane under nitrogen was cooled in a dry ice/acetone bath to −78° C. Pentafluorosulfanyl isocyanate (2.3 g, 0.014 mole) was condensed into the flask, a dry ice condenser with drierite tube was attached, and the flask was allowed to warm to room temperature. After 24 hours, the volatiles were removed and the solid residue was stirred with hexanes to yield 4.4 g (96%) a of white solid, mp 65°–68° C. Crystallization from chloroform raised the melting point to 67°–69° C.; $^1$H NMR (CDCl$_3$): 3.55 (t, 2H), 4.70 (t, 2H), 7.78 (broad s, 1H); IR (KBr): 3260 (NH), 1765 (C=O), 1625, 1600 (NO$_2$), 1505 (amide II), 950–860 (SF$_5$) cm$^{-1}$.

Anal. Calcd for C$_4$H$_5$F$_5$N$_4$O$_8$S: C, 13.19; H, 1.38; F, 26.09; N, 15.38; S, 8.80. Found: C, 13.28; H, 1.34; F, 25.98; N, 15.41; S, 9.02.

EXAMPLE 4

N-Pentafluorosulfanyl-2-fluoro-2,2-dinitroethyl carbamate

Pentafluorosulfanyl isocyanate (2.0 g, 0.012 mole) was condensed onto 3.9 g (0.025 mole) of 2-fluoro-2,2-dinitroethanol and 20 ml of dry 1,2-dichloroethane at −78° C. A dry ice condenser with drierite tube was attached and the flask was allowed to warm to room temperature. After 5 hours, the condenser was removed and the flask was tightly stoppered. After 24 hours at room temperature, a sample removed for NMR analysis showed the reaction was not complete. After 45 hours the volatiles were removed to give a semisolid residue which was stirred with 25 ml of water to yield 2.85 g (75%) of white solid, mp 80°–82° C. Crystallization (chloroform) gave mp 81°–83° C.; $^1$H NMR (CDCl$_3$): 5.35 (d, 3H), 7.82 (broad s, 1H); IR (KBr): 3240 (NH), 1765 (C=O), 1610 (NO$_2$), 1515 (amide II), 970–860 (SF$_5$) cm$^{-1}$.

Anal. Calcd for C$_3$H$_3$F$_6$N$_3$O$_6$S: C, 11.15; H, 0.94; F, 35.28; N, 13.00; S, 9.92. Found: C, 11.03; H, 0.92; F, 36.42; N, 13.12; S, 10.27.

EXAMPLE 5

N-Pentafluorosulfanyl-2,2,2-trinitroethyl carbamate

Pentafluorosulfanyl isocyanate (0.40 g, 0.0024 mole) was condensed at −78° C. onto a mixture of 0.85 g (0.0047 mole) of 2,2,2-trinitroethanol and 5 ml of acetonitrile. The mixture was allowed to warm to room temperature for 24 hours before the volatiles were removed and the residue was stirred with 15 ml of water to give 0.78 g (93%) of solid, mp 88°–90° C. Crystallization from chloroform-hexane gave mp 89°–90° C.; $^1$H NMR (CDCl$_3$): 5.55 (s, 2H), 7.85 (broad s, 1H); IR (KBr): 3295 (NH), 1610 (NO$_2$), 1515 (amide II), 990°850 (SF$_5$) cm$^{-1}$.

Anal. Calcd for C₃H₃F₅N₄O₈S: C, 10.29; H, 0.86; F, 27.13; N, 16.00; S, 9.16. Found: C, 10.45; H, 0.81; F, 26.80; N, 15.27; S, 9.32.

EXAMPLE 6

N-(Pentafluorosulfanyl)-N'-(2-fluoro-2,2-dinitroethyl-)urea

Pentafluorosulfanyl isocyanate (0.8 g, 0.0047 mole) was condensed at −78° C. into a solution of 0.8 g (0.0052 mole) of 2-fluoro-2,2-dinitroethylamine in 30 ml of methylene chloride. The solution was allowed to warm to room temperature for 3 hours before the volatiles were removed to yield 1.3 g (86%) of solid (mp 135°–137° C.) which was recrystallized from acetone-chloroform to give mp 139°–140° C.; ¹H NMR (acetone-d₆): 4.85 (pair of d, 2H), 6.85 (broad, 1H), 10.3 (broad, 1H); IR (KBr): 3380, 3300 (NH), 1695 (C=O), 1615 (NO₂), 1555 (amide II), 950–860 (SF₅) cm⁻¹.

EXAMPLE 7

N,N'-Bis(pentafluorosulfanyl)-2,2,-dinitropropane-1,3-dicarbamate

On to a mixture of 1.0 g (0.006 mole) of 2,2-dinitropropane-1,3-diol and 20 ml of 1,2-dichloroethane cooled to −78° C. was condensed 2.4 g (0.014 mole) of pentafluorosulfanyl isocyanate. The reaction mixture was then stirred at room temperature and the progress of the reaction was monitored by NMR analysis. The reaction rate was slow due in part to the low solubility of the diol in dichloroethane. After 6 days the reaction rate slowed to near zero and an additional 2.4 g (0.014 mole) of isocyanate was added. After an additional 6 days at room temperature, the insoluble solid [2.5 g (83%), mp 160°–163° C.)] was removed by filtration and recrystallized from hot dichloroethane to yield 2.2 g, mp 161°–163° C.; ¹H NMR (acetone-d₆): 5.33 (s); IR (KBr): 3270 (NH), 1770 (C=O), 1595 (NO₂), 1510 (amide II), 950–860 (SF₅ cm⁻¹.

Anal. Calcd for C₅H₆F₁₀N₄O₈S₂: C, 11.91; H, 1.20; F, 37.68; N, 11.11; S, 12.72. Found: C, 11.88: H, 1.28; F, 37.54; N, 11.06; S, 12.98.

EXAMPLE 8

N,N'-Bis(pentafluorosulfanyl)-2,2,8,8-tetranitro-4,6-dioxanonane-1,9-dicarbamate A solution of 1.0 g (0.0029 mole) of 2,2,8,8-tetranitro-4,6-dioxanonane-1,9-diol in 8 ml of acetonitrile was cooled in a dry ice/acetone bath while 1.2 g (0.0071 mole) of pentafluorosulfanyl isocyanate was condensed into the flask. The mixture was allowed to warm to room temperature for 20 hours after which the volatiles were removed to give 2.0 g (100%) of solid, mp 135°–137° C. Crystallization from methylene chloride gave 1.85 g, mp 138°–139° C.; ¹H NMR (acetone-d₆): 4.72 (s, 4H), 5.05 (s, 2H), 5.32 (s, 4H); IR (KBr): 3290 (NH), 1770 (C=O), 1590 (NO₂), 1510 (amide II), 950–850 (SF₅) cm⁻¹.

Anal. Calcd for C₉H₁₂F₁₀N₆O₁₄S₂: C, 15.84; H, 1.77; F, 27.84; N, 12.32; S, 9.40. Found: C, 15.89; H, 1.81; F, 28.05; N, 12.28; S, 9.72.

EXAMPLE 9

N,N'-Bis(pentafluorosulfanyl)-3,6-dinitrazaoctane-1,8-dicarbamate

A mixture of 68 g (0.286 mole) of 3,6-dinitrazaoctane-1,8-diol and 500 ml of acetonitrile in a 1 liter 3-neck round bottom flask (equipped with a dry ice condenser and drierite tube) was stirred in a dry ice/acetone bath. When the temperature of the mixture was near the freezing point of acetonitrile (−48° C.), pentafluorosulfanyl isocyanate (98.4 g, 0.582 mole) was condensed into the flask over a 45 minute period (near the end of the addition, the mixture became too thick with precipitate to stir). The mixture was allowed to warm to room temperature at which time all material had dissolved into solution. After 20 hours, the volatiles were removed on a rotary evaporator until crystals began to precipitate from the solution. Dichloroethane (200 ml) was added and the mixture was cooled to −15° C. and filtered to give 155.1 g of crystals, mp 144°–146° C. An additional 8.50 g of essentially pure product was recovered from the filtrate raising the yield to 163.6 g (99%). ¹H NMR (acetone-d₆): 4.27 (s overlap with t, 8H), 4.55 (t, 4H); IR (KBr): 3290 (NH), 1750 with shoulder at 1770 (C=O), 1520, 1500 (NO₂ and amide II), 960–830 (SF₅), cm<¹.

Anal. Calcd for C₈H₁₄F₁₀N₆O₈S₂: C, 16.67; H, 2.45; F, 32.96; N, 14.58; S, 11.13. Found: C, 16.84; H, 2.40, F, 32.54; N, 14.48; S, 11.32.

EXAMPLE 10

N,N-Bis(pentafluorosulfanyl)-3-nitraza-5,5-dinitrooctane-1,8-dicarbamate

Pentafluorosulfanyl isocyanate (0.55 g, 0.0033 mole) was condensed onto a mixture of 0.30 g (0.0011 mole) of 3-nitraza-5,5-dinitrooctane-1,8-diol and 5 ml of acetonitrile. After 20 hours at room temperature, the volatiles were removed to give 0.66 g (100%) of solid. Crystallization from dichloroethane gave 0.60 g, mp 140°–141° C.; ¹H NMR (acetone-d₆): 1.87 (m, 2H), 2.85 (CH₂ overlap NH, 4H), 4.35 (overlapping CH₂ groups, 4H) 4.60 (t, 2H), 5.23 (s, 2H); IR (KBr): 3230 (broad, NH), 1750, shoulder at 1770 (C=O), 1570, shoulder at 1590 (NO₂), 1515 (amide II), 960–830 (SF₅) cm⁻¹, Anal. Calcd for C₉H₁₄F₁₀N₆O₁₀S₂: C, 17.42; H, 2.27; F, 30.63; N, 13.55; S, 10.34. Found: C, 17.39; H, 2.26; F, 30.80; N, 13.58; S, 10.67.

Obviously, numerous modifications and variations of the present invention are possible in light of the above teachings. It is therefore to be understood that within the scope of the appended claims the invention may be practiced otherwise than as specifically described herein.

What is claimed and desired to be secured by Letters Patent of the United States is:

1. A pentafluorosulfonyl polynitroaliphatic compound of the formula

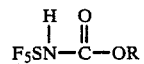

wherein R is selected from the group consisting of —CH₂C(NO₂)₂CH₃, —CH₂CH₂C(NO₂)₃, —CH₂CF(NO₂)₂; and —CH₂C(NO₂)₃.

2. The compound according to claim 1 which is N-pentafluorosulfanyl-2,2-dinitropropyl carbamate of the formula, F₅SNHCOOCH₂C(NO₂)₂CH₃.

3. The compound according to claim 1 which is N-pentafluorosulfanyl-3,3,3-trinitropropyl carbamate of the formula, F₅SNHCOOCH₂CH₂C(NO₂)₃.

4. The compound according to claim 1 which is N-pentafluorosulfanyl-2-fluoro-2,2-dinitroethyl carbamate of the formula, F₅SNHCOOCH₂CF(NO₂)₂.

5. The compound according to claim 1 which is N-pentafluorosulfanyl-2,2,2-trinitroethyl carbamate of the formula, F₅SNHCOOCH₂C(NO₂)₃.

* * * * *